US005591438A

United States Patent [19]
Olson et al.

[11] Patent Number: 5,591,438
[45] Date of Patent: Jan. 7, 1997

[54] NATAMYCIN RECOVERY

[75] Inventors: Phillip T. Olson, Manitowoc; James R. Millis, Kohler; Michael H. Reimer, Sheboygan, all of Wis.

[73] Assignee: Bio-Technical Resources L.P., Manitowoc, Wis.

[21] Appl. No.: 237,473

[22] Filed: May 3, 1994

Related U.S. Application Data

[63] Continuation-in-part of Ser. No. 121,142, Sep. 17, 1993, abandoned, and Ser. No. 121,145, Sep. 17, 1993, abandoned, which is a continuation-in-part of Ser. No. 623,585, Dec. 7, 1990, abandoned.

[51] Int. Cl.$^6$ .................................................. A61K 35/78
[52] U.S. Cl. ........................... 424/195.1; 514/31; 536/6.5; 536/16.9; 536/124
[58] Field of Search ........................... 424/195.1; 514/31; 536/6.5, 16.9, 18.5, 124, 127

[56] References Cited

U.S. PATENT DOCUMENTS

| | | | |
|---|---|---|---|
| 3,378,441 | 4/1968 | Bridger | 514/31 |
| 3,892,850 | 7/1975 | Struyk et al. | 424/119 |
| 4,006,222 | 2/1977 | Metzger | 424/123 |
| 4,308,375 | 12/1981 | Tang | 536/17 R |
| 5,231,014 | 7/1993 | Eisenschink et al. | 435/76 |

FOREIGN PATENT DOCUMENTS

| | | |
|---|---|---|
| 844289 | 8/1960 | United Kingdom . |
| 846933 | 9/1960 | United Kingdom . |
| 9210580 | 6/1992 | WIPO . |
| 9303170 | 2/1993 | WIPO . |
| 9303171 | 2/1993 | WIPO . |

*Primary Examiner*—John Kight
*Assistant Examiner*—Howard C. Lee
*Attorney, Agent, or Firm*—Bruce M. Monroe

[57] ABSTRACT

A process for the recovery of high purity natamycin from fermentaion broth by extraction with methanol is disclosed. In one embodiment the process comprises the steps:

(1) adding methanol to a natamycin feed stream comprising at least 2 g/L of solid suspended natamycin to form an extraction medium, and maintaining the extraction medium at a temperature of 0°–25° C., preferably not over 15° C.;

(2) adjusting the pH of the extraction medium to 1.0 to 4.5 while maintaining the temperature at 0°–25° C. for 0.5 to 30 hours, but preferably not over 0.5 hours when the temperature is 15°–25° C.;

(3) removing solids from the extraction medium to form an extraction liquor;

(4) raising the pH of the extraction liquor to 6.0–9.0; and (5) recovering precipitated natamycin.

20 Claims, No Drawings

NATAMYCIN RECOVERY

CROSS-REFERENCE TO RELATED APPLICATIONS

This application is a continuation-in-part of U.S. patent applications Ser. Nos. 08/121,142, now abandoned, and 08/121,145, now abandoned, each of which was filed Sep. 17, 1993, and each of which was a continuation-in-part of U.S. patent application Ser. No. 07/623,585, now abandoned, filed on Dec. 7, 1990, each of which is incorporated herein by reference.

FIELD OF THE INVENTION

This invention relates to a rapid, inexpensive process for recovering natamycin from fermentation broth.

BACKGROUND OF THE INVENTION

Natamycin (also known as pimaricin or tenecetin) is a well known antibiotic (Florey, "Analytical Profiles of Drug Substances", Vol. 10, 1981; Merck Index, 8th ed., "Pimaricin", p. 834). Although its valuable antibiotic properties have been recognized, there has been little research or commercialization of natamycin because of the extremely high cost of its manufacture. Because of its solubility in various liquids, natamycin recovery processes have not been economic. A need exists for an economic natamycin recovery process.

Natamycin has been prepared by fermentation, such as disclosed in U.K. Patent 846,933 using *Streptomyces gilvosporeus*. In this process, natamycin is recovered by methanol extraction followed by tedious steps of adsorption and elution. Penick, U.S. Pat. No. 3,378,441, discloses recovery of natamycin by salting it out of the fermentation broth, extracting with methanol, removing the solids, and then evaporating the liquid. Struyk, U.S. Pat. No. 3,892,850, discloses recovery of natamycin by extraction with acidified butanol followed by distillation and precipitation. Struyk also discloses calcium chloride dissolved in methanol to improve natamycin solubility. Each of these processes require an expensive recovery step, such as adsorption and elution, distillation, or evaporation. U.K. Patent No. 844,289 shows the precipitation of natamycin from acetic acid by the addition of water.

SUMMARY OF THE INVENTION

High purity natamycin can be recovered from a fermentation broth containing natamycin by extraction with methanol under controlled pH and temperature conditions. The process comprises the steps:
(1) adding methanol to a natamycin feed stream comprising at least 2 g/L of solid suspended natamycin to form an extraction medium, and maintaining the extraction medium at a temperature of 0°–25° C., preferably not over 15° C.;
(2) adjusting the pH of the extraction medium to 1.0 to 4.5 while maintaining the temperature at 0°–25° C. for 0.5 to 30 hours, but preferably not over 0.5 hours when the temperature is 15°–25° C.;
(3) removing solids from the extraction medium to form an extraction liquor;
(4) raising the pH of the extraction liquor to 6.0–9.0; and
(5) recovering precipitated natamycin.
In another embodiment the process comprises the steps of:
(1) adding methanol containing about 10–50 g/L of a solubility enhancing salt to a natamycin feed stream comprising at least 2 g/L of solid suspended natamycin to form an extraction medium;
(2) removing solids from the extraction medium to form an extraction liquor;
(3) adding water to the extraction liquor to precipitate the natamycin; and
(4) recovering precipitated natamycin.

In either embodiment, higher purity natamycin can be obtained (1) by washing the precipitated natamycin recovered in the last step with water, (2) by treating the extraction liquor with activated carbon prior to precipitation of the natamycin, or (3) by a combination of these steps. The preferred solubility enhancing salt is calcium chloride.

DETAILED DESCRIPTION OF THE INVENTION

Methanol Extraction

Natamycin Fermentation Broth Feed Stream

Natamycin production by fermentation is described in Eisenschink, U.S. Pat. No. 5,231,014, U.K. Patent 846,933, and U.S. patent applications Ser. Nos. 07/740,545 and 07/740,536, both filed on Aug. 5, 1991. The fermentation broth produced in these fermentations comprises solid suspended natamycin, biomass and water. The process disclosed by Eisenschink, for example, typically produces broth containing about 7–12 g/L of natamycin.

The broth is used as the feed stream for the recovery process, either directly, or after concentration by removal or some or nearly all the water. The feed stream should contain at least 2 g of natamycin per liter, but higher concentrations are preferred. Since the broth comprises water, solid suspended natamycin, and biomass solids, some, or substantially all, of the water can be removed by any convenient conventional solid/liquid separation technique, such as, centrifugation, filtration, or decantation (see, Example 1, which exemplifies filtration). If desired, the solids can be further dried by conventional means such as with warm air, by spray-drying, or by pressing water out by mechanical means. If the solids are dried by heating, a temperature of about 20°–80° C. should be used. Temperatures above 95° C. should be avoided.

The solubility of natamycin in the extraction medium (feed stream and methanol) decreases as the water increases. Since water content of the extraction medium depends on the amount of water in the feed stream, it is desirable to remove as much water as possible from the feed stream before Step 1. If the feed stream contains about 70% by volume water, about three times as much methanol is required than when starting with a substantially dry feed stream. If the feed stream contains about 40% by volume water, about twice as much methanol is required.

The solids content of the feed stream may be as low as about 20% by weight or less, if little or no water is removed, or, if water is removed, as high as about 98% by weight. To achieve the natamycin concentration required for high recovery, it may be necessary to concentrate the broth before addition of methanol. Depending on equipment availability, particularly for methanol recovery, it may be desirable to remove substantially all of the water from the broth before addition of methanol. This minimizes the amount of methanol needed for recovery. If economics dictate, most of the water should be removed from the broth. This allows the process to be carried out at higher pH without extensive by-product formation. In a preferred embodiment, water removal produces a feed stream that contains at least 50% by weight solids.

Methanol Addition

In Step 1, methanol is added to the feed stream. Under the proper conditions natamycin has excellent solubility in this inexpensive solvent, and simple techniques for methanol recovery are available. For optimum natamycin recovery, sufficient methanol is added to the feed stream to produce an extraction medium that contains about 20–150 g natamycin per liter. Since natamycin tends to precipitate out of the acidified extraction medium at high concentrations (Step 2), a concentration of 20–120 g natamycin per liter of extraction medium is preferred.

Acid Addition

In Step 2, the pH of the extraction medium is adjusted to about 1.0–4.5 by the addition of an acid. This renders the natamycin highly soluble in the extraction medium. Hydrochloric acid is an excellent acid, although any conventional compatible acidic material may be used. Though not a preferred technique, Steps 1 and 2 could be combined by adding the acid directly to the methanol.

Formation of natamycin methyl ester, an undesired by-product, depends on the pH, the natamycin-methanol contact time, and the temperature (see Table 1). It is important that this step be carried out at a temperature of about 0°–25° C., since formation of natamycin methyl ester and other undesirable by-products is minimized. The higher the temperature or the longer the contact time, the greater the by-product production at a given pH. To avoid excessive natamycin methyl ester formation at 15°–25° C., short contact times, i.e., 0.5 hr or less, should be used. At about 15° C., the extraction time should not exceed about 1.5 hr. An extraction temperature of about 0°–15° C. is preferred.

In general, at a pH near 2 and at about 0° C., extraction can be continued for about 12 hr without excessive by-product formation. At about 25° C., extraction should be discontinued after about 0.5 hr. As the pH is increased toward 4.5, longer times are acceptable. At a pH near 4 and a temperature of about 4° C., the time can be about 30 hours.

TABLE 1

Natamycin Methyl Ester Formation in Methanol

| Temp (°C.) | pH | Time (hr) | Natamycin (g/L) | Methyl Ester (% by weight of product) |
| --- | --- | --- | --- | --- |
| 23 | 2.4 | 0 | 44 | 0 |
| " | " | 1 | 42 | 3.9 |
| " | " | 2 | 41 | 7.3 |
| " | " | 3 | 38 | 9.7 |
| 23 | 3.2 | 0 | 38 | 0 |
| " | " | 1 | 38 | 2.3 |
| " | " | 2 | 37 | 3.9 |
| " | " | 4 | 34 | 7.4 |
| " | " | 6 | 32 | 9.2 |
| | | 16 | 23 | 14 |
| 23 | 4.0 | 0 | 41 | 0 |
| " | " | 2 | 40 | 2.3 |
| " | " | 4 | 39 | 3.7 |
| 4 | 2.4 | 0 | 42 | 0.4 |
| " | " | 2 | 42 | 1.3 |
| " | " | 8.5 | 39 | 2.7 |
| " | " | 19 | 37 | 5.2 |

For commercially acceptable production, it is desirable to keep the methyl ester content below about 5% by weight of the total product (natamycin, methyl ester and any impurities), and preferably below about 3% by weight. It is possible to conduct the methanol extraction at the necessary low temperature by cooling the stream and/or the methanol so that the extraction medium is in the low temperature range at the time of acid addition.

The proper time/temperature/pH relationship for extraction can readily be ascertained by trial, noting the times and temperatures that will give the desired product purity at a particular pH, and bearing in mind the optimum economics for the particular equipment being used.

The pH depends to some extent on the water content of the extraction medium and the yield desired. To obtain a precipitation yield of about 90% or more, the natamycin concentration in the extraction medium should be about 40 g/L. In the absence of water this requires a pH of about 4.5. At about 30% water/70% methanol (by volume) this requires a pH of about 2.5 (Table 2).

TABLE 2

Solubility of Natamycin in Methanol and Methanol/Water Mixtures

| Water Content (%) | pH | Natamycin (g/L) |
| --- | --- | --- |
| 0 | 7.0 | 6 |
| " | 4.5 | 50 |
| " | 3.8 | 78 |
| " | 2.0 | 94 |
| 30 | 7.0 | 4 |
| " | 3.3 | 18 |
| " | 2.4 | 55 |

Removal of Suspended Solids

In Step 3, the remaining suspended solids are removed by any convenient solid/liquid separation technique, such as filtration or centrifugation leaving an extraction liquor. After being removed from the extraction medium, the solids may still contain a significant quantity of natamycin. Accordingly, in a preferred embodiment, the solids are washed with methanol or with a mixture of methanol and water to recover at least a portion of the natamycin contained in the solids. The wash solution is added to the extraction liquor.

Natamycin Precipitation and Recovery

In Step 4, any compatible basic material can be used to raise the pH of the extraction liquor to about 6.0–9.0. This causes precipitation of high purity natamycin, which is removed and dried. Typical useful, inexpensive and compatible basic materials are sodium and potassium hydroxides. If desired, water may also be added in Step 4 to assist in natamycin precipitation. This may be preferable where the feed stream has a high concentration of natamycin and a small amount of water. The remaining liquid by-product (residual liquid) which contains valuable natamycin, fermentation residues, methanol, inorganic salts and water is sent to methanol recovery. Methanol can be recovered by conventional distillaion techniques for solvent recovery.

The process produces natamycin of at least about 80% by weight purity and often at least about 90% by weight purity. In a preferred embodiment, the natamycin precipitate that is recovered in Step 5 is washed with water and then dried resulting in natamycin of at least about 90% by weight purity.

The process can be carried out effectively by batch extraction. However, for large scale commercial extraction, a continuous process may be preferred. In one technique natamycin fermentation broth, preferably concentrated to a low water content, is continuously fed to a mixer and thoroughly mixed with methanol at low temperature. The pH is controlled by the addition of acid and natamycin rapidly dissolves. The resulting extraction medium is then fed to a filter to separate the cell mass and other solids from the extraction liquor. The extraction liquor is fed to a crystallizer operating at a higher pH and the natamycin precipitates. The precipitated natamycin and residual liquid are continuously removed from the crystallizer. Extraction time, water content, temperature and pH can be adjusted for economical production of the natamycin.

Addition of a Solubility Enhancing Salt

Rapid high recovery of natamycin is also possible without addition of acid to lower the pH followed by addition of base to raise the pH and precipitate the natamycin. In this process a mixture of methanol and a solubility enhancing salt is mixed with the natamycin fermentation broth feed stream (with or without concentration). The resulting extraction medium is filtered to remove the cell mass and other solids and produce an extraction liquor. Water is added to the extraction liquor to precipitate natamycin.

Any salt that increases the solubility of natamycin in methanol under the extraction conditions and does not react with or otherwise interfere with natamycin extraction, recovery or product purity may be used. Calcium chloride ($CaCl_2$) is the preferred solubility enhancing salt. It is most effective in amounts of about 10–50 g/L salt per liter of methanol.

For optimum natamycin recovery, water is typically removed from the feed stream as described above. The feed streams should contain enough natamycin so that, after the extraction liquid (methanol/salt solution) is added to the feed stream, the resulting extraction medium contains at least 2 g/L of natamycin. When the concentration of natamycin is less than 2 g/L, it is difficult to precipitate natamycin by addition of water.

To precipitate a high percentage of the natamycin, the water content of the extraction liquor should be increased to at least 50% by volume. Table 3 indicates the solubility of natamycin in a methanol/water/calcium chloride solution as a function of water content.

TABLE 3

Solubility of Natamycin in Methanol/$CaCl_2$*
Extractant at Various Water Concentrations

| Water Content (%, v/v) | Natamycin (g/L) |
| --- | --- |
| 0 | 91 |
| 10 | 44 |
| 20 | 19 |
| 30 | 6 |
| 40 | 5 |
| 50 | 2 |

*20 g/L $CaCl_2$.

This process can be run at pH 2–9, preferably at pH 6–8. If the pH is low, shorter extraction times should be used because acidic conditions promote natamycin methyl ester formation. (See Table 4) If the pH is above 6, ester formation is slower. Any reasonable temperature may be used (i.e. 20°–30° C.).

TABLE 4

Ester Formation in Methanol with 40 g/L $CaCl_2$

| Temp (°C.) | pH | Time (hr) | Natamycin (g/L) | Methyl Ester (% of product) |
| --- | --- | --- | --- | --- |
| 23 | 4.4 | 0 | 72 | 0 |
|  |  | 6 | 67 | 5.0 |
| 23 | 5.3 | 0 | 51 | 0 |
|  |  | 20 | 48 | 2.4 |
| 23 | 6.1 | 0 | 51 | 0 |
|  |  | 20 | 49 | 1.1 |
| 5 | 4.4 | 0 | 60 | 0 |
|  |  | 8 | 60 | 0.5 |

In Step (a), a methanol/salt solution is added to the feed stream. In Step (b), the remaining suspended solids are removed from the extraction medium by any convenient solid/liquid separation technique, such as filtration or centrifugation, to obtain an extraction liquor. The solids may still contain a significant quantity of natamycin and may be washed with methanol or a mixture of methanol and water to recover at least a portion of the natamycin contained in the solids. The methanol wash solution is added to the extraction liquor. In Step (c), water is added to the extraction liquor to precipitate natamycin. In Step (d) the precipitated natamycin is recovered. The recovered precipitate contains at least 80% by weight natamycin and usually at least 85% by weight natamycin. Higher purity product, up to at least 90% by weight natamycin, can be obtained by washing the precipitate recovered in Step (d) with water or by treating the extraction liquor with activated carbon prior to Step (c) or by a combination of these steps.

INDUSTRIAL APPLICABILITY

The process is a rapid, inexpensive process for the recovery of natamycin from fermentation broth, especially from broths that contain well over 2 g/L natamycin.

All of the literature, patents and patent applications mentioned in this application are incorporated herein by reference.

EXAMPLE 1

This example illustrates natamycin recovery using controlled conditions of pH and temperature. Fermentation broth containing natamycin, biomass, water and minor quantities of nutrients and impurities, prepared as described in Eisenschink, U.S. Pat. No. 5,231,014, Example Test #1, was concentrated to about 45% by weight solids by filtration on a Buchner funnel. Celite® 545 was added to enhance filtration. The filter cake contained about 7.5% by weight natamycin.

About 74 g of filter cake was mixed with about 96 mL of methanol to form an extraction medium slurry and the temperature of the slurry was reduced to about 4° C. with an ice-bath jacket. Hydrochloric acid was added to the slurry to reduce the pH to about 2.4 and the slurry was held for about 3 hr at this temperature and pH.

The slurry was filtered on a Buchner funnel and about 105 mL of clear liquid (extraction liquor) containing about 40 g/L natamycin was obtained. The pH of the extraction liquor was raised to about 7 by addition of 5N sodium hydroxide solution and held at this pH with mild stirring for about 1 hr. During this time a thick white precipitate formed.

The precipitate was isolated by filtration and dried at about 40° C. under vacuum. About 4.1 g of dry product was obtained. The product was about 92% by weight natamycin (anhydrous basis) and 1.7% by weight methyl ester.

EXAMPLE 2

This example illustrates natamycin recovery using a controlled pH and temperature conditions. The process of Example 1 was repeated except that the temperature of the extraction medium was about 22° C. instead of about 4° C. About 3.9 g of dry product was obtained after drying. The product was about 83% by weight natamycin (anhydrous basis) and 10% by weight methyl ester.

EXAMPLE 3

This example illustrates natamycin recovery using a solubility enhancing salt. Fermentation broth was concentrated to 45% by weight solids by filtration on a Buchner funnel. Celite® 545 was added to enhance the filtration rate. The filter cake was further dried to 98% by weight solids at 60° C. in a fluid bed dryer. The natamycin content of the dried cake was 18% by weight.

40 g of dried cake was added to a solution of 3 g calcium chloride in 150 mL of methanol, and the slurry was mixed for 30 min. The slurry was filtered on a Buchner funnel and the clear filtrate (extraction liquor) collected.

The water content of the filtrate was increased to 30% by volume by slowly adding water while stirring. A thick off-white precipitate formed. The precipitate was separated by filtration, washed with water, and dried at 30° C. in vacuum. The precipitate was 88% by weight natamycin (anhydrous basis).

EXAMPLE 4

This example illustrates natamycin recovery using a solubility enhancing salt. Fermentation broth (1 L) was heated to 70° C. for 15 min, cooled to room temperature, and allowed to settle. 500 mL of the upper layer was decanted and discarded. The remaining solids were concentrated by filtration on a Buchner funnel. 20 g Celite® 545 was added to increase filtration rate. The filter cake was washed twice with 50 mL methanol to remove most of the water and leave about 10% by weight water. The filter cake was 9% by weight natamycin. 40 g of filter cake was added to a solution of 2 g calcium chloride in 50 mL of methanol and mixed for 0.5 hr. The slurry was filtered on a Buchner funnel and the clear filtrate (extraction liquor) collected. 3 g of activated charcoal was added to the filtrate and the mixture was stirred for 1 hr. The charcoal was removed by filtration and the clear filtrate was collected.

The water content of the filtrate was increased to 50% by volume by slowly adding water with stirring. A thick white precipitate formed which was filtered, washed with water, and dried at 30° C. in vacuum. The precipitate was 95% by weight natamycin (anhydrous basis).

What is claimed is:

1. A process for the recovery of natamycin from natamycin fermentation broth comprising in order the following steps:

(1) adding methanol to a natamycin feed stream comprising biomass, water, and at least 2 g/L of solid suspended natamycin to form an extraction medium, and maintaining the extraction medium at a temperature of 0°–25° C.;

(2) adjusting the pH of the extraction medium to 1.0 to 4.5 while maintaining the temperature at 0°–25° C. for 0.5–30 hours;

(3) removing solids from the extraction medium to form an extraction liquor;

(4) raising the pH of the extraction liquor to 6.0–9.0; and (5) recovering the precipitated natamycin.

2. The process of claim 1 in which the feed stream contains at least 50% by weight solids.

3. The process of claim 1 in which the temperature of the extraction medium is maintained at 0°–15° C.

4. The process of claim 1 in which steps 1 and 2 are combined by adding acid to the methanol before step (1).

5. The process of claim 1 additionally comprising, following step (3) and before step (4):

(6) washing the solids with methanol and adding the methanol to the extraction liquor.

6. The process of claim 1 additionally comprising, before step (4), the step of:

(7) treating the extraction liquor with activated carbon.

7. The process of claim 1 additionally comprising, before step 1, the step of:

(8) removing water from the natamycin feed stream so that the natamycin feed stream comprises less than 10% by weight water.

8. The process of claim 7 in which the extraction medium contains 20–150 g of natamycin per liter.

9. The process of claim 8 in which the temperature of the extraction medium is maintained at 0°–15° C.

10. The process of claim 9 in which temperature of the extraction medium is maintained at 0°–15° C. for 0.5–1.5 hours.

11. The process of claim 10 additionally comprising, before step (4), the step of:

(7) treating the extraction liquor with activated carbon.

12. A process for the recovery of natamycin from natamycin fermentation broth comprising in order the following steps:

(1) adding methanol containing about 10–50 g/L of a solubility enhancing salt to a natamycin feed stream comprising biomass, water, and at least 2 g/L of solid suspended natamycin to form an extraction medium;

(2) removing solids from the extraction medium to form an extraction liquor;

(3) adding water to the extraction liquor to precipitate the natamycin; and (4) recovering the precipitated natamycin.

13. The process of claim 12 in which the solubility enhancing salt is calcium chloride.

14. The process of claim 13 in which the feed stream contains at least 50% by weight solids.

15. The process of claim 13 additionally comprising, before step (3), the step of:

(7) treating the extraction liquor with activated carbon.

16. The process of claim 13 additionally comprising, before step 1, the step of:

(6) removing water from the natamycin feed stream so that the natamycin feed stream comprises less than 10% by weight water.

17. The process of claim 16 in which the extraction medium contains 20–150 g of natamycin per liter.

18. The process of claim 17 additionally comprising, before step (3), the step of:

(7) treating the extraction liquor with activated carbon.

19. A process for the recovery of natamycin from natamycin fermentation broth comprising in order the following steps:

(1) adding methanol to a natamycin feed stream comprising biomass, water, and solid suspended natamycin to form an extraction medium containing 20–250 g of natamycin per liter, and maintaining the extraction medium at a temperature of less than 15° C.;

(2) adjusting the pH of the extraction medium to 1.0 to 4.5 while maintaining the temperature at 0°–15° C. for less than 1.5 hours;

(3) removing solids from the extraction medium to form an extraction liquor;

(4) raising the pH of the extraction liquor to 6.0–9.0; and (5) recovering the precipitated natamycin.

20. The process of claim 19 in which steps 1 and 2 are combined by adding acid to the methanol before step 1.

* * * * *